(12) United States Patent
Vogtmeier et al.

(10) Patent No.: US 9,903,827 B2
(45) Date of Patent: Feb. 27, 2018

(54) HANDLING MISALIGNMENT IN DIFFERENTIAL PHASE CONTRAST IMAGING

(71) Applicant: KONINKLIJKE PHILIPS N.V., Eindhoven (NL)

(72) Inventors: Gereon Vogtmeier, Aachen (DE); Udo Van Stevendaal, Ahrensburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 364 days.

(21) Appl. No.: 14/420,108

(22) PCT Filed: Aug. 9, 2013

(86) PCT No.: PCT/IB2013/056524
§ 371 (c)(1),
(2) Date: Feb. 6, 2015

(87) PCT Pub. No.: WO2014/027289
PCT Pub. Date: Feb. 20, 2014

(65) Prior Publication Data
US 2015/0212017 A1    Jul. 30, 2015

Related U.S. Application Data

(60) Provisional application No. 61/684,199, filed on Aug. 17, 2012.

(51) Int. Cl.
*G01N 23/04* (2006.01)
*G01N 23/20* (2018.01)
(Continued)

(52) U.S. Cl.
CPC ....... *G01N 23/20075* (2013.01); *A61B 6/484* (2013.01); *A61B 6/582* (2013.01);
(Continued)

(58) Field of Classification Search
CPC ....... A61B 6/025; A61B 6/4441; A61B 6/484; A61B 6/502; A61B 6/582; A61B 6/587;
(Continued)

(56) References Cited

U.S. PATENT DOCUMENTS 5,812,629 A    9/1998  Clauser
2011/0243300 A1  10/2011  Kaneko et al.
(Continued)

FOREIGN PATENT DOCUMENTS

EP        1731099 A1    12/2006
WO    2011070521 A1     6/2011

*Primary Examiner* — Irakli Kiknadze

(57) ABSTRACT

The present invention relates to handling misalignment in differential phase contrast imaging. In order to provide an improved handling of misalignment in X-ray imaging systems for differential phase contrast imaging, an X-ray imaging system (10) for differential phase contrast imaging is provided that comprises a differential phase contrast setup (12) with an X-ray source (14), an X-ray detector (16), and a grating arrangement comprising a source grating (18), a phase grating (20) and an analyzer grating (22). The source grating is arranged between the X-ray source and the phase grating, and the analyzer grating is arranged between the phase grating and the detector. Further, the system comprises a processing unit (24), and a measurement system (26) for determining a misalignment of at least one of the gratings. The X-ray source and the source grating are provided as a rigid X-ray source unit (28). The phase grating, the analyzer grating and the detector are provided as a rigid X-ray detection unit (30). The measurement system is an optical measurement system configured to determine a misalignment between the differential phase contrast setup consisting of the X-ray source unit and the X-ray detection unit. Further, the processing unit is configured to provide a correction signal (34) based on the determined misalignment.

20 Claims, 4 Drawing Sheets

(51) Int. Cl.
*A61B 6/00* (2006.01)
*G21K 1/06* (2006.01)
*A61B 6/02* (2006.01)

(52) U.S. Cl.
CPC ............ *A61B 6/587* (2013.01); *G01N 23/04* (2013.01); *G21K 1/067* (2013.01); *A61B 6/025* (2013.01); *A61B 6/4441* (2013.01); *A61B 6/502* (2013.01); *G01N 2223/323* (2013.01)

(58) Field of Classification Search
CPC ....... A61B 6/4291; A61B 6/4035; A61B 6/06; A61B 6/032; A61B 6/4233; A61B 6/482; A61B 6/505; A61B 6/4007; A61B 6/4241; A61B 6/4258; A61B 6/5235; A61B 6/483; A61B 6/508; A61B 6/00; A61B 6/04; A61B 6/404; G01N 2223/323; G01N 23/04; G01N 23/20075; G21K 1/067; H05B 6/68; H05B 6/80; G02B 27/14; G02B 27/143; H01S 3/005
USPC .......................................... 378/62, 205, 206
See application file for complete search history.

(56) References Cited

U.S. PATENT DOCUMENTS

| | | | | |
|---|---|---|---|---|
| 2012/0057677 | A1* | 3/2012 | Vogtmeier | G02B 5/1857 378/85 |
| 2014/0270070 | A1* | 9/2014 | Spahn | A61B 6/484 378/62 |

* cited by examiner

HANDLING MISALIGNMENT IN DIFFERENTIAL PHASE CONTRAST IMAGING

CROSS-REFERENCE TO PRIOR APPLICATIONS

This application is the U.S. National Phase application under 35 U.S.C. § 371 of International Application Serial No. PCT/IB2013/056524, filed on Aug. 9, 2013, which claims the benefit of U.S. Application Ser. No. 61/684,199, filed on Aug. 17, 2012. These applications are hereby incorporated by reference herein.

FIELD OF THE INVENTION

The present invention relates to handling misalignment in differential phase contrast imaging, and relates in particular to an X-ray imaging system for differential phase contrast imaging, a method for handling misalignment in an X-ray imaging system for differential phase contrast imaging, to a computer program element, and to a computer readable medium.

BACKGROUND OF THE INVENTION

Differential phase contrast imaging, also referred to as DPCI, is becoming a promising X-ray imaging modality, for example for mammography. In order to be able to use conventional X-ray tubes providing incoherent X-ray radiation, an absorption grating to produce partly coherent X-ray light waves is provided in relation with the X-ray source, which is why the term "source grating" is used, or G0. Further, a phase grating, or G1, is provided to generate a phase shift between adjacent beams and a further absorption grating G2, also referred to as analyser grating, that is provided to analyse the phase information resulting from the investigated object. Such an arrangement is described, for example, in EP 1 731 099 A1. It has been shown that the grating arrangement has to be adjusted quite accurately in orders of nanometers. However, it has been shown that misalignment occurs, in particular in larger structures, leading to disadvantages in the receivable results.

SUMMARY OF THE INVENTION

Thus, there is a need to provide an improved handling of misalignment in X-ray imaging systems for differential phase contrast imaging.

The object of the present invention is solved by the subject-matter of the independent claims, wherein further embodiments are incorporated in the dependent claims.

It should be noted that the following described aspects of the invention apply also for the X-ray imaging system, the method for handling misalignment in an X-ray imaging system for differential phase contrast imaging, as well as to the computer program element and the computer readable medium.

According to a first aspect of the present invention, an X-ray imaging system for differential phase contrast imaging is provided, comprising a differential phase contrast setup with an X-ray source, an X-ray detector, and a grating arrangement comprising a source grating, a phase grating, and an analyser grating. The source grating is arranged between the X-ray source and the phase grating, and the analyser grating is arranged between the phase grating and the detector. Further, a processing unit and a measurement system is provided, wherein the measurement system is provided for determining a misalignment of at least one of the gratings. The X-ray source and the source grating are provided as a rigid X-ray source unit, wherein the phase grating, the analyser grating, and the detector are provided as a rigid X-ray detection unit. The measurement system is an optical measurement system configured to determine a misalignment between the differential phase contrast setup consisting of the X-ray source unit and the X-ray detection unit. The processing unit is configured to provide a correction signal based on the determined misalignment.

The term "misalignment" relates to deviations in the distance and also deviations in the inclination of the components to each other.

According to an exemplary embodiment, the measurement system comprises at least three sensors at different corners of the X-ray detection unit.

According to an exemplary embodiment, the at least three sensors are provided as at least three 4-quadrant photodiodes. An optical source device is fixedly attached to the X-ray source unit configured to generate a light beam to each of the 4-quadrant photodiodes. The 4-quadrant photodiodes measure the movement in the plane of the detector and an angular tilt with respect to the light beam.

In an example, one or more optical sources are provided in combination with optical arrangements such as lenses, for example for focussing, combined with photodiodes.

The term "optical" refers to visible light. The 4-quadrant photodiodes, also referred to as matrix or array of photodiodes, are provided as a sensitive device for measuring misalignment by weighting of intensity profile that is shifted with the movement. A further approach is to provide an interferometer for the phase measurement, e.g. a so-called Michelson laser interferometer. The segmentation of the diode allows a measurement of the "centre of light intensity" and also the deviation in x- or y-direction. This allows the measurement and calculation of the position movement.

According to an exemplary embodiment, at least three sensors are provided as an interferometer for the phase measurement of an optical source device, which is fixedly attached to the X-ray source unit configured to generate a light beam to each of the interferometers.

According to an exemplary embodiment, the optical source is configured to provide the optical signal in form of a modulated signal. The interferometers are configured to detect optical phase shift. For a phase analysis, it is provided i) a correlation unit configured to correlate the signals from all interferometers, and/or ii) a coupling unit configured to in-coupling of the light to optical fibres at the corners and measuring the phase shift by an interferometer setup and/or a timing analysis unit, and/or iii) a measuring unit configured to measure the intensity shifts of the 4-quadrant photodiode and correlate the signals from all 4-quadrant photodiodes.

The 4-quadrant photodiodes measure the movement by intensity weighting of the shift beam, e.g. using also sensitivity increasing options by geometry adaption for amplification of the position sensitivity. For example, four 4-quadrant photodiodes are provided as a 4-quadrant photodiode matrix sensor.

According to an exemplary embodiment, the optical source device is provided as a single light source generating a single beam. Splitting means are provided for splitting the single beam into at least three sub-beams.

For example, the splitting means comprise a) an integrated optical mirror system; and/or b) a fibre unit with lenses at the end and a split unit at the entrance.

According to an exemplary embodiment, actuators are provided for moving and aligning at least one grating of the X-ray source unit and/or at least one grating of the X-ray detection unit. The processing unit is configured to compute activation signals for the actuators based on the correction signal, and to transfer the activation signals to the actuators.

For example, the whole source unit or grating unit is moved and aligned.

According to an exemplary embodiment, the actuators are provided as i) piezo actuators, and/or ii) motor-driven micrometer-screws. The actuators provide a movement in the range of approximately 1 micrometer up to approximately 10 millimeters. The actuators provide an alignment accuracy of approximately 1 micrometer, for example.

According to an exemplary embodiment, a correction unit is provided for correcting the data provided by the detector for further computation steps, wherein the processing unit is configured to compute correction factors based on the correction signal, and to transfer the correction factors to the correction unit for an evaluating computation for providing the final results. The correction unit may be provided as a software correction by the processing unit. The actuator approach can also be combined with the correction approach, mentioned above. For example, the misalignment is corrected to a part or degree of it, and the other part of misalignment is accepted.

According to an exemplary embodiment, a moving arrangement for a relative movement between an object under examination and at least one of the gratings is provided. For example, the moving arrangement is provided as a stepping arrangement for stepping at least one of the gratings of the interferometer unit in the respective grating plane. In another example, an object support is provided and a relative movement between the object support and the differential phase contrast setup is provided. The gratings are provided in a constant alignment to each other during a scan for at least one image acquisition. According to one sub-example, the object support is provided stationary, and the differential phase contrast setup is moved in a direction transverse to an X-ray direction. In a second sub-example, the differential phase contrast setup is provided stationary, and the object support is moved in a direction transverse to the X-ray direction.

According to a second aspect of the present invention, a method for handling misalignment in an X-ray imaging system for differential phase contrast imaging is provided, comprising the following steps:
a) In a first step, a differential phase contrast setup with an X-ray source, an X-ray detector, a processing unit, and a grating arrangement comprising a source grating, a phase grating, and an analyser grating is provided. The source grating is arranged between the X-ray source and the phase grating, and the analyser grating is arranged between the phase grating and the detector. The X-ray source and the source grating are provided as a rigid X-ray source unit. The phase grating, the analyser grating, and the detector are provided as a rigid X-ray detection unit.
b) In a second step, a misalignment of at least one of the gratings with an optical measurement system is determined.
c) In a third step, a correction signal is computed based on the determined misalignment.

According to an exemplary embodiment, activation signals for actuators are computed, based on the correction signal in step d1). In a further step d2), the activation signals are transferred to actuators for moving and aligning the X-ray source unit and/or the X-ray detection unit. In step d3), the X-ray source unit and/or the X-ray detection unit are moved and aligned.

According to an exemplary embodiment, as a further step e1), correction factors are computed, based on the correction signal. Further, in a step e2), a transferring of the correction factors to a correction unit is provided for correcting the data provided by the detector for further computational steps. Still further, it is provided for evaluating computing the data provided by the detector for providing the final results considering the correction factors in a step e3).

According to an aspect of the present invention, an optical measurement system is provided for determining exact values of the misalignment in the x-y-z-plane, including the rotations ($\delta$-$\tau$-$\phi$; delta-theta-phi). Further, as a first approach, the adjustment to the optimum position of the interferometer unit with the phase grating, G1, and the analyser grating, G2, with respect to the source grating, G0, is done with the help of precise actuators, for example piezo actuators. In a further approach, a software correction is applied to the acquired scan data with the information of the actual misalignment of the system at the dedicated acquisition data set. In order to continuously monitor or track the position deviation of the gratings, an optical method of measuring the relative movement of, for example, all four corners of the detection unit (including the interferometer G1-G2) relative to the G0-X-ray source unit with very precision could give comparable correction information. According to a further aspect, a combination of a position sensitive device and an interferometric approach with transmission time/phase shift detection of the optical signal could provide precise position information. 4-quadrant photodiodes, or matrix sensors, are provided in each corner of the detection unit, for example, to measure the x-y-movement and also an angular tilt with respect to the X-ray source. For example, a split of a beam can be done via an integrated optical mirror system or simply by using a fibre unit with lenses at the end and a split unit at the entrance. The 4-quadrant detector (photodiode) measures a movement by intensity weighting of the shifted beam (using also sensitivity increasing options by geometry adaptation for amplification of the position sensitivity. For increased sensitivity of the distance variation, an analysis of the phase information of the optical signal may be beneficial, as the optical phase shift of the modulated optical signal could be directly correlated to the distance information. The phase analysis could be done either by correlating the signals from the 4-quadrant detectors at the four corners, or by in-coupling of the light to optical fibres at the corners and measuring the phase shift by an interferometer setup or/and a timing analysis unit. The requirements for the temporal resolution are directly depending on the system geometry and might be different for Microdose systems (owned by Philips), tomosynthesis setups, C-arm-based systems, and CT-like geometries.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
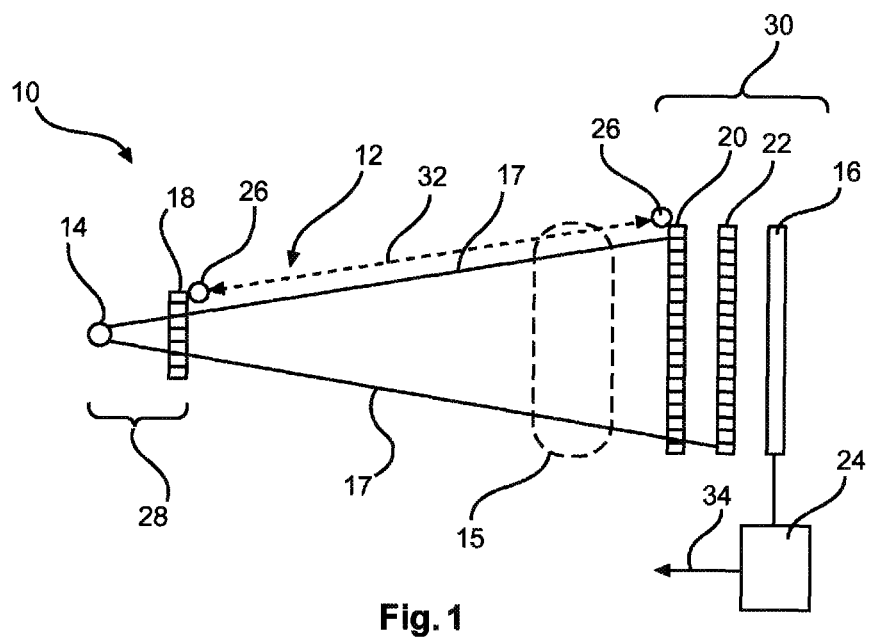
FIG. 1 shows a first example of an X-ray imaging system for differential phase contrast imaging in a schematic setup.

FIG. 1 shows an X-ray imaging system 10 for differential phase contrast imaging, comprising a differential phase contrast setup 12 with an X-ray source 14, an X-ray detector 16, and a grating arrangement comprising a source grating 18, a phase grating 20, and an analyser grating 22. The source grating 18 is arranged between the X-ray source 14 and the phase grating 20, and the analyser grating 22 is arranged between the phase grating 20 and the detector 16. Further, a processing unit 24, and a measurement system 26 for determining a misalignment of at least one of the gratings is provided. The X-ray source and the source grating are provided as a rigid X-ray source unit 28, and the phase grating, the analyser grating, and the detector are provided as a rigid X-ray detection unit 30. It must be noted that the rigid attachments or mounting features are not further shown. The measurement system 26 is an optical measurement system configured to determine a misalignment between the differential phase contrast setup consisting of the X-ray source unit 28 and the X-ray detection unit 30. This is indicated by a dotted double-arrow 32. The processing unit 24 is configured to provide a correction signal 34, based on the determined misalignment. An object is indicated with dotted line 15, arranged between the source grating 18 and the phase grating 20. Further, lines 17 indicate an X-ray beam provided by the X-ray source 14.

Figure 2:
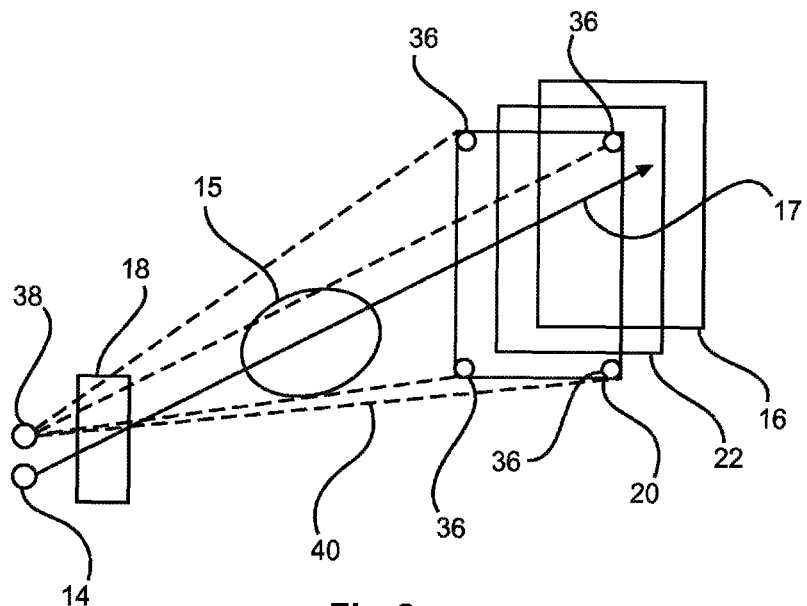
FIG. 2 shows a further example of a setup for an X-ray imaging system.

In an example, the measurement system comprises at least three sensors 36 at different corners of the X-ray detection unit. For example, FIG. 2 shows an embodiment with four sensors 36 at the corners of the X-ray detection unit. For example, at least three sensors are provided as at least three 4-quadrant photodiodes. An optical source device 38 is fixedly attached to the X-ray source unit 28, for example to the X-ray source 14, configured to generate a light beam, indicated with dotted line 40, to each of the 4-quadrant photodiodes. The 4-quadrant photodiodes measure the movement in the plane of the detector and an angular tilt with respect to the light beam.

According to a further example, the at least three sensors are provided as an interferometer for the phase measurement of an optical source device (not further shown), which is fixedly attached to the X-ray source unit configured to generate the light beam to each of the interferometers.

According to a further example, although not further shown, the optical source is configured to provide the optical signal in form of a modulated signal, and the interferometers are configured to detect optical phase shift. For a phase analysis, it is provided a correlation unit configured to correlate the signals from all interferometers. As an addition, or alternative, it is further provided a coupling unit configured to in-coupling of the light to optical fibres at the corners and measuring the phase shift by an interferometer setup and/or a timing analysis unit. Still further, as an addition, or alternative, it is provided a measuring unit configured to measure the intensity shifts of the 4-quadrant photodiode and correlate the signals from all 4-quadrant photodiodes.

Figure 3:
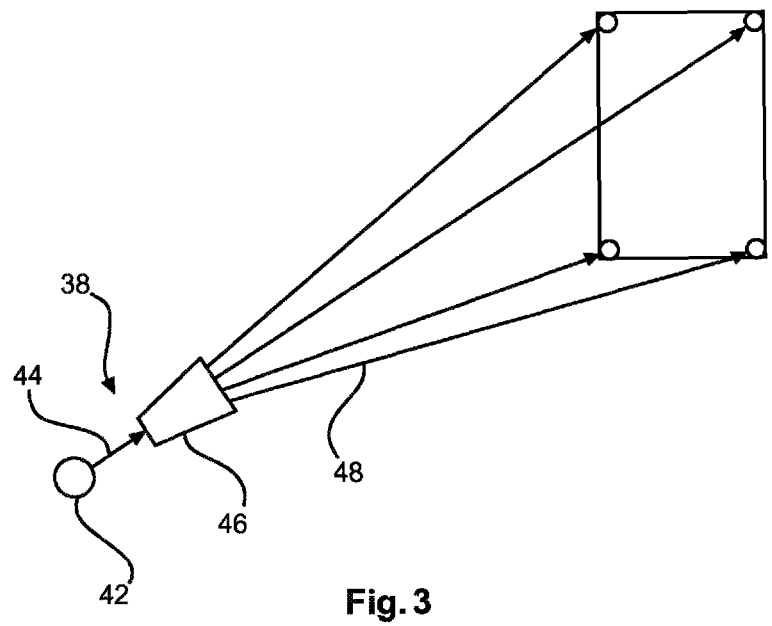
FIG. 3 shows an example for an optical measuring system.

As shown in FIG. 3, the optical source 38 can be provided as a single light source 42, generating a single beam 44. Splitting means 46 are provided for splitting the single beam into at least three sub-beams, for example four sub-beams 48. The splitting means 40 may comprise an integrated optical mirror system, and/or a fibre unit with lenses at the end and a split unit at the entrance.

Figure 4:
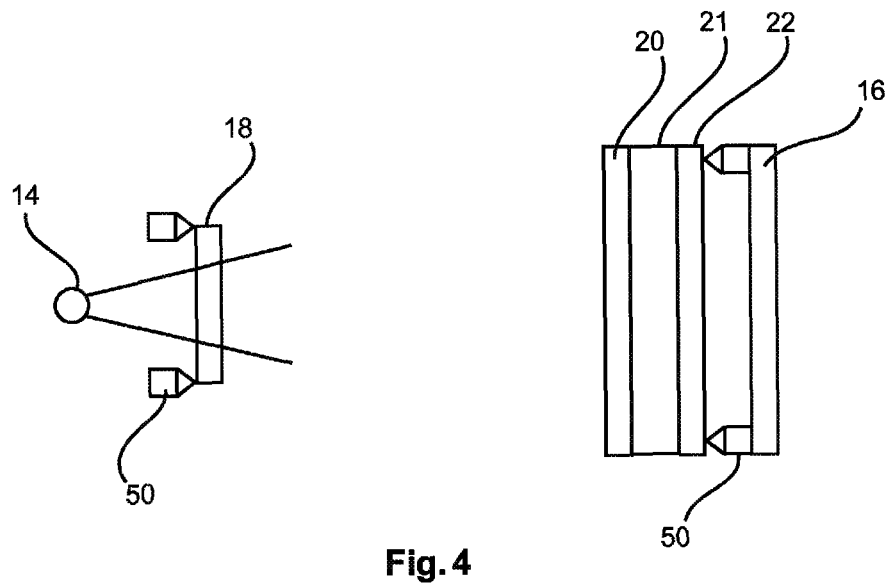
FIG. 4 shows a further example for an X-ray imaging system.

According to a further example, shown in FIG. 4, actuators 50 are provided for moving and aligning at least one grating of the X-ray source unit 28, and/or at least one grating of the X-ray detection unit 30. The processing unit is configured to compute activation signals for the actuators based on the correction signal, and to transfer the activation signals to the actuators. For example, the whole source unit or grating unit is moved and aligned.

Figure 5:
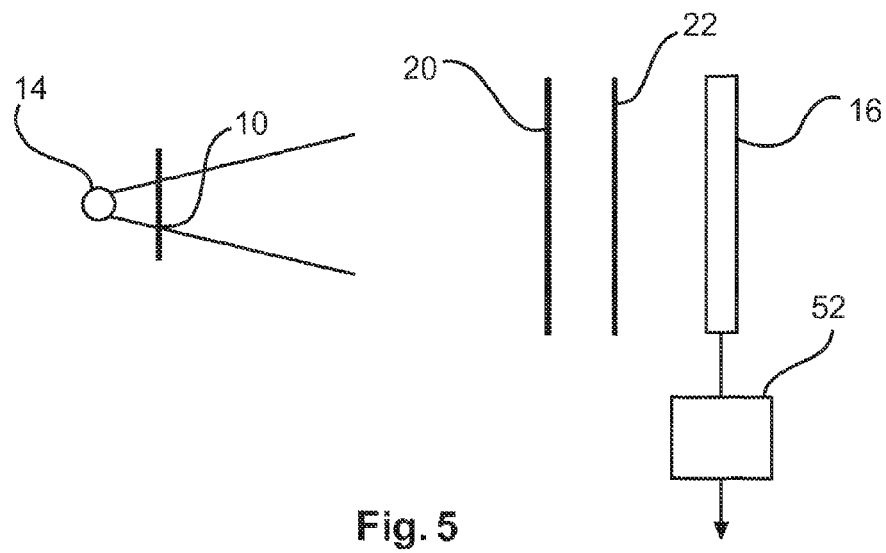
FIG. 5 shows a further setup of an X-ray imaging system.

FIG. 5 shows the actuators 50 in relation with the source grating 18 and the X-ray source 14.

Further, FIG. 4 also indicates the X-ray detection unit 30 with the analyser grating 22 and the X-ray detector 18. The actuators are provided as piezo actuators, and/or motor-driven micrometer-screws. Both are provided with a movement in the range of approximately 1 micrometer up to approximately 10 millimeters.

As shown in FIG. 5, a correction unit 52 may be provided for correcting the data provided by the detector for further computation steps. The processing unit 52 is configured to compute correction factors based on the correction signal, and to transfer the correction factors to the correction unit for an evaluating computation for providing the final results.

According to a further example (not further shown), a moving arrangement for a relative movement between an object under examination and at least one of the gratings is provided for the so-called phase stepping. According to a first example, the moving arrangement is provided as a stepping arrangement for stepping at least one of the gratings of the interferometer unit in the respective grating plane. According to a second example, an object support is provided and a relative movement between the object support and the differential phase contrast setup. The gratings are provided in a constant alignment to each other during a scan for at least one image acquisition. For this purpose, it is either the object support provided stationary, and the differential phase contrast setup is moved in a direction transverse to an X-ray direction, or the differential phase contrast setup is provided stationary, and the object support is moved in a direction transverse to the X-ray direction.

For example, a mammography arrangement is provided, in which a breast is compressed or held between two supporting surfaces, and a detector is rotated around the X-ray tube, together with the grating structure, which is also moving.

Figure 6:
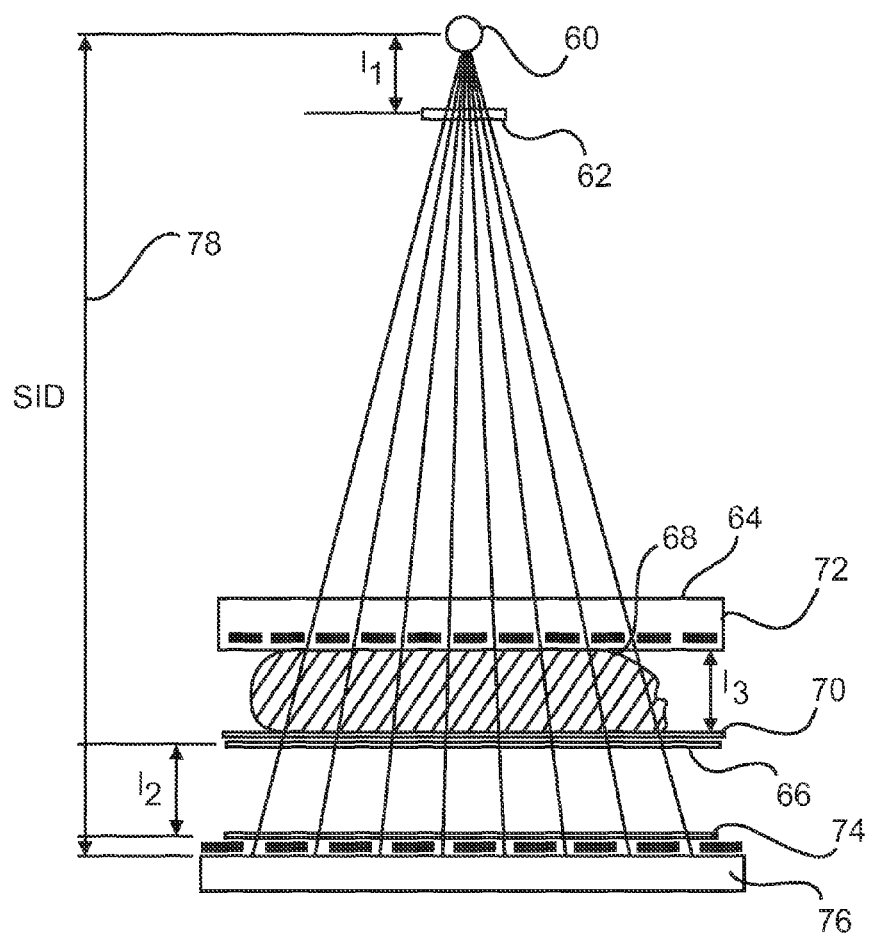
FIG. 6 shows a further example of an X-ray imaging system.

For example, FIG. 6 shows an X-ray source 60, followed by a source grating 62, or grating G0. Further, a pre-collimator 64 is provided in front of a phase grating 66, G1. As further shown, a breast 68 may be compressed between a first breast support 70, in front of the phase grating 66, and the pre-collimator 64 acting as a second support 72. Further, an analyser grating 74, G2, is provided in front of a detector 76. For example, the X-ray source 60 and the source grating 62 are provided in a distance L1 of approximately 50 millimeters. Still further, the first and second breast supports are provided with a distance L2. The phase grating 66 and the analyser gratings are provided in a distance L3. Still further, the overall distance from the source 60 to the detector 76 is referred to as SID (source image distance) and can be provided with 660 millimeters. Still further, the distance between the source grating 62 and the grating G1 is provided to be 470 millimeters. Length L1, as well as L3, can be provided to be 50 millimeters. The distance between the breast support 70 and the second breast layer, i.e. distance L2, is referred to as Talbot distance.

Figure 7:
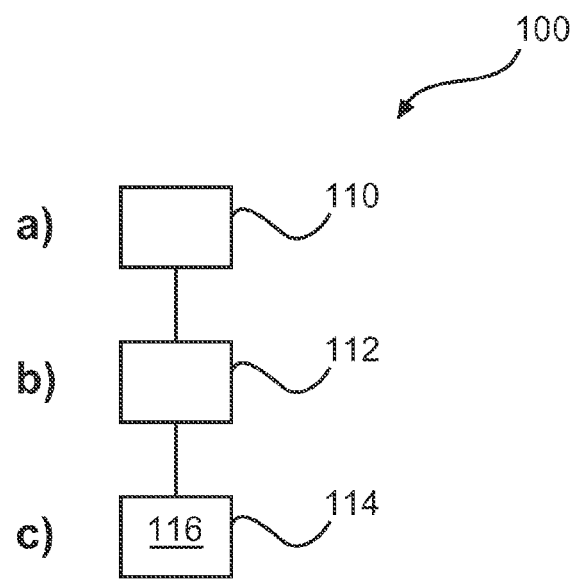
FIG. 7 shows basic steps of a method for handling misalignment in an X-ray imaging system for differential phase contrast imaging according to a first example.

Further, as shown in FIG. 7, a method 100 for handling misalignment in an X-ray imaging system for differential phase contrast imaging is provided, comprising the following steps: In a first step 110, a differential phase contrast setup is provided with an X-ray source, an X-ray detector, a processing unit, and a grating arrangement, comprising a source grating, a phase grating, and an analyser grating. The source grating is arranged between the X-ray source and the phase grating, and the analyser grating is arranged between the phase grating and the detector. The X-ray source and the source grating are provided as a rigid X-ray source unit. The phase grating, the analyser grating, and the detector are provided as a rigid X-ray detection unit. In a second step 112, a misalignment of at least one of the gratings is determined with an optical measurement system. In a third step 114, a correction signal 116 is computed, based on the determined misalignment.

The first step 110 is also referred to as step a), the second step 112 as step b), and the third step 114 as step c).

Figure 8:
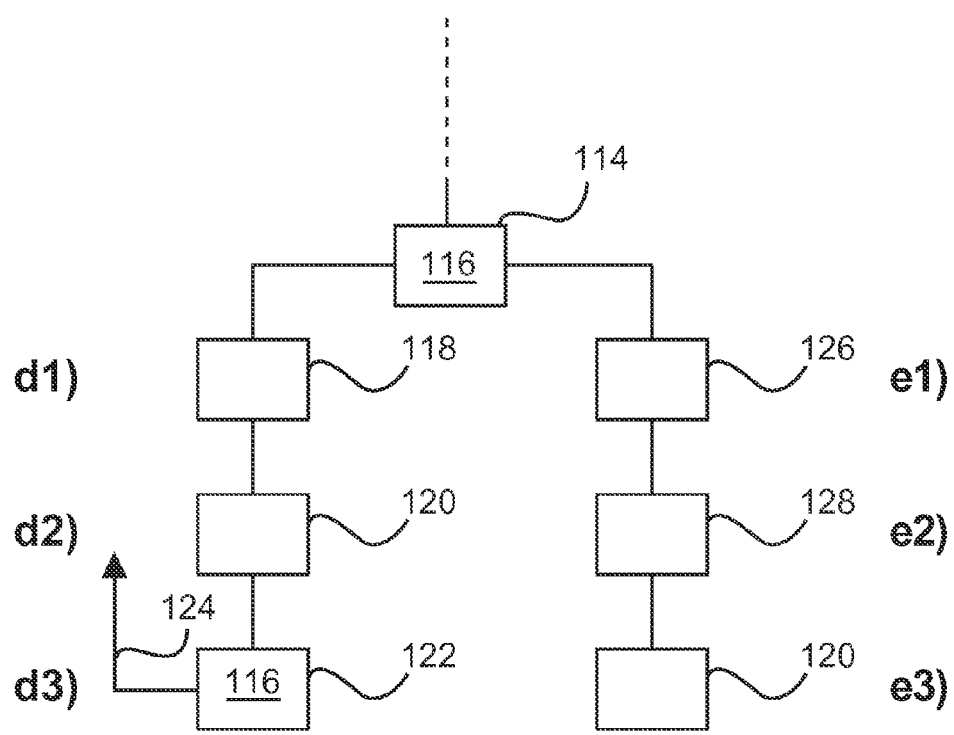
FIG. 8 shows further steps of examples of methods for handling misalignment in an X-ray imaging system for differential phase contrast imaging.

According to a further example of the method of FIG. 7, step d1) is provided, in which activation signals for actuators are computed 118, based on the correction signal. In a step d2), the activation signals are transferred 120, to actuators for moving and aligning the X-ray source unit and/or the X-ray detection unit. In a further step d3), the X-ray source unit and/or the X-ray detection unit are moved and aligned 122. The further use of the detected misalignment can be provided to different further purposes, as indicated with reference numeral 124. These are shown in FIG. 8.

As a further example the following is provided. It is noted that although the following is shown in FIG. 8 in combination with the above-mentioned features, the following is also provided independent of the above-mentioned example. In a first step e1), correction factors are computed 126, based on the correction signal. In a further step e2), the correction factors are transferred 128 to a correction unit provided for correcting the data provided by the detector for further computation steps. In a still further step e3), the data provided by the detector for providing the final results considering the correction factors, are evaluated and computed in a further step 130.

According to the above-mentioned examples, the differential phase contrast imaging unit is integrated in an existing mammography system, or in an existing C-arm system, CT apparatus or tomosynthesis scanner. As a further example, the above-mentioned embodiments are applied or integrated into the so-called micro-dose system by Philips. For example, the interferometer unit consisting of gratings G1 and G2 is placed directly in front of the detector, and the X-ray beam passes the compressed breast before entering the interferometer. While this unit can be manufactured quite stable, regarding the alignment of the gratings G1 and G2 to each other, a fixed and stable alignment of G0 is almost impossible. The mechanical system design of a differential phase contrast system with moving components like in a Microdose system, or C-arm, CT or tomosynthesis system can thus be aligned by the above described examples. Therefore, for example, it is provided for an alignment of the X-ray source unit with the grating G0 to the interferometer unit with the gratings G1 and G2, in order to be very precise and stable for all conditions during operation. Due to providing an optical measurement system, it is not necessary to apply extra X-ray dosage for so-to-speak calibrating an alignment of an X-ray system.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An X-ray imaging system for differential phase contrast imaging, comprising
    a differential phase contrast setup that includes:
    an X-ray source;
    an X-ray detector; and
    a grating arrangement comprising a source grating, a phase grating and an analyzer grating, wherein the source grating is arranged between the X-ray source and the phase grating, and the analyzer grating is arranged between the phase grating and the detector;
    a processing unit; and
    a measurement system for determining a misalignment of at least one of the gratings;
    wherein the X-ray source and the source grating are provided as a rigid X-ray source unit and wherein the phase grating, the analyzer grating and the detector are provided as a rigid X-ray detection unit;
    wherein the measurement system is an optical measurement system configured to determine a misalignment of the differential phase contrast setup between the X-ray source unit and the X-ray detection unit;
    wherein the processing unit is configured to provide a correction signal based on the determined misalignment;
    wherein the measurement system comprises at least three sensors at different corners of the X-ray detection unit;
    wherein the at least three sensors are provided as at least three 4-quadrant photodiodes;
    wherein an optical source device fixedly attached to the X-ray source unit is configured to generate a light beam to each of the 4-quadrant photodiodes; and
    wherein the 4-quadrant photodiodes measure the movement in the plane of the detector and an angular tilt with respect to the light beam.

2. An X-ray imaging system according to claim 1, wherein the at least three sensors are each provided as an interferometer for the phase measurement of said optical source device fixedly attached to the X-ray source unit and configured to generate a light beam to each of the interferometers.

3. An X-ray imaging system according to claim 2, wherein the optical source device is configured to provide an optical signal in form of a modulated signal; and
    the interferometers are configured to detect optical phase shift;
    wherein for a phase analysis, at least one of the following i), ii), and iii) is provided:
    i) a correlation unit configured to correlate the signals from all interferometers;
    ii) a coupling unit configured for in-coupling of the light to optical fibers at the corners and measuring the phase shift by at least one of an interferometer setup and a timing analysis unit;
    iii) a measuring unit configured to measure the intensity shifts of the 4-quadrant photodiode and correlate the signals from all 4-quadrant photodiodes.

4. An X-ray imaging system according to claim 2,
    wherein the optical source device is provided as a single light source generating a single beam; and
    wherein splitting means are provided for splitting the single beam into at least three sub-beams directed respectively to said at least three 4-quadrant photodiodes.

5. An X-ray imaging system according to claim 1, further comprising actuators configured for moving and aligning at least one grating of the X-ray source unit; at least one grating of the X-ray detection unit; or both at least one grating of the X-ray source unit and at least one grating of the X-ray detection unit; and
    wherein the processing unit is configured to compute activation signals for the actuators based on the correction signal and to transfer ones of the activation signals to the actuators.

6. An X-ray imaging system according to claim 5, wherein the actuators are provided as:
    i) piezo actuators;
    ii) motor-driven micrometer-screws; or
    iii) a mixture from among i) and ii),
        wherein both the piezo actuator and the motor-driven micrometer-screw provide a movement in the range of approximately 1 micrometer up to approximately 10 millimeters.

7. An X-ray imaging system according to claim 1,
    further comprising a correction unit configured for correcting data provided by the detector for further computation steps,
    wherein the processing unit is configured to compute correction factors based on the correction signal and to transfer ones of the correction factors to the correction unit for an evaluating computation for providing the final results; and
    wherein said data to be corrected is acquired by X-ray applied to an object under examination.

8. An X-ray imaging system according to claim 1,
    wherein a moving arrangement for a relative movement between an object under examination and at least one of the gratings is provided; and
    wherein the X-ray imaging system features at least one of i) and ii) which are as follows:
    i) the moving arrangement is provided as a stepping arrangement for stepping at least one of the gratings of an interferometer unit in the respective grating plane, said interferometer unit comprising the gratings of the X-ray dectection unit;
    ii) an object support is provided and a relative movement between the object support and the differential phase contrast setup; wherein the gratings are provided in a constant alignment to each other during a scan for at least one image acquisition; and wherein;
    ii1) the object support is provided stationary and the differential phase contrast setup is moved in a direction transverse to an X-ray direction; or
    ii2) the differential phase contrast setup is provided stationary and the object support is moved in a direction transverse to the X-ray direction.

9. The X-ray imaging system of claim 1, wherein the determining of misalignment is from output of the at least three sensors.

10. The X-ray imaging system of claim 1, wherein a cross-section of said X-ray detection unit has a periphery; and wherein, said at least three 4-quadrant photodiodes are spaced apart along said periphery.

11. A method for handling misalignment in an X-ray imaging system for differential phase contrast imaging, comprising the following steps:
   a) providing a differential phase contrast setup with an X-ray source, an X-ray detector, a processing unit, and a grating arrangement comprising a source grating, a phase grating and an analyser grating, wherein the source grating is arranged between the X-ray source and the phase grating, and the analyser grating is arranged between the phase grating and the detector; wherein the X-ray source and the source grating are provided as a rigid X-ray source unit; and wherein the phase grating, the analyser grating and the detector are provided as a rigid X-ray detection unit;
   b) determining a misalignment of at least one of the gratings with an optical measurement system, wherein the measurement system comprises at least three sensors at different corners of the X-ray detection unit, wherein the at least three sensors are provided as at least three 4-quadrant photodiodes, wherein an optical source device fixedly attached to the X-ray source unit is configured to generate a light beam to each of the 4-quadrant photodiodes, and wherein the 4-quadrant photodiodes measure the movement in the plane of the detector and an angular tilt with respect to the light beam;
   c) computing a correction signal based on the determined misalignment.

12. A non-transitory computer readable medium having stored thereon a computer program for handling misalignment in an X-ray imaging system for differential phase contrast imaging, said computer program having instructions executable by a processor for performing a plurality of acts, from among said plurality there being the acts of:
   i) for a differential phase contrast setup that includes an X-ray source, an X-ray detector, a processing unit, and a grating arrangement comprising a source grating, a phase grating and an analyzer grating; wherein the source grating is arranged between the X-ray source and the phase grating, and the analyzer grating is arranged between the phase grating and the detector; wherein the X-ray source and the source grating are provided as a rigid X-ray source unit; wherein the phase grating, the analyzer grating and the detector are provided as a rigid X-ray detection unit; wherein an optical measurement system for determining a misalignment of at least one of the gratings comprises at least three sensors at different corners of the X-ray detection unit; and wherein the at least three sensors are provided as at least three 4-quadrant photodiodes, an optical source device being fixedly attached to the X-ray source unit,
   generating by said optical source device, a light beam to each of the 4-quadrant photodiodes, wherein 4-quadrant photodiodes measure the movement in the plane of the detector and an angular tilt with respect to the light beam,
   determining, from the measurement by the 4-quadrant photodiodes, a misalignment of the differential phase contrast setup between said X-ray source unit and said X-ray detection unit; and
   computing a correction signal based on the determined misalignment.

13. The non-transitory computer readable medium of claim 12, wherein from among said plurality there are the further acts of:
   computing, based on the correction signal, actuator activation signals for moving at least one of said X-ray source unit, as a whole, and said X-ray detection unit, as a whole, into mutual alignment of said X-ray source unit, as a whole, with said X-ray detection unit as a whole; and
   transferring, to an actuator configured for said moving into mutual alignment, a signal from among the computed actuator activation signals.

14. The non-transitory computer readable medium of claim 12, wherein a cross-section of said X-ray detection unit has a periphery; and wherein, said at least three 4-quadrant photodiodes are spaced apart along said periphery.

15. An X-ray imaging system for differential phase contrast imaging, comprising
   a differential phase contrast setup that includes:
   an X-ray source;
   an X-ray detector;
   a grating arrangement comprising a source grating, a phase grating and an analyzer grating, wherein the source grating is arranged between the X-ray source and the phase grating, and the analyzer grating is arranged between the phase grating and the detector; wherein the X-ray source and the source grating are provided as a rigid X-ray source unit and wherein the phase grating, the analyzer grating and the detector are provided as a rigid X-ray detection unit a cross-section of which has a periphery, said X-ray detection unit having corners along said periphery;
   an optical measurement system that comprises at least three sensors spaced apart along said periphery, said sensors being at different ones of said corners of the X-ray detection unit, wherein each of the sensors has a surface for receiving light, said surface divided into quadrants for separate light measurements per quadrant, an optical source device fixedly attached to said X-ray source being configured for generating a light beam to the surfaces of each of said at least three sensors, wherein said optical measurement system is configured to determine, from output of said at least three sensors, a misalignment of at least one of the gratings, as to movement in the plane of the detector and as to angular tilt with respect to the X-ray source; and
   a processing unit configured to provide a correction signal based on the determined misalignment.

16. The X-ray imaging system of claim 15, wherein the at least three sensors are provided as at least three 4-quadrant photodiodes, said optical source device being configured to generate said light beam to each of the 4-quadrant photodiodes, wherein the 4-quadrant photodiodes measure movement in the plane of the detector and an angular tilt with respect to the X-ray source.

17. The X-ray imaging system of claim 15, further comprising an actuator configured for moving at least one of said X-ray source unit and said X-ray detection unit;
   wherein said processing unit is further configured to:

compute, based on the correction signal, actuator activation signals for moving at least one of said X-ray source unit, as a whole, and said X-ray detection unit, as a whole, into mutual alignment of said X-ray source unit, as a whole, with said X-ray detection unit as a whole; and transfer, to said actuator, a signal from among the computed actuator activation signals.

18. The X-ray imaging system of claim 15, wherein the at least three sensors are each provided as an interferometer for phase measurement of said optical source device, wherein said optical source device is configured to generate a light beam to each of the interferometers.

19. The X-ray imaging system of claim 18, wherein said optical source device is configured to provide an optical signal in form of a modulated signal; and the interferometers are configured to detect optical phase shift;

wherein for a phase analysis, at least one of i), ii), and iii) is provided, wherein i), ii), and iii) are as follows:

i) a correlation unit configured to correlate the signals from all interferometers;

ii) a coupling unit configured for in-coupling of the light to optical fibers at the corners and measuring the phase shift by at least one of an interferometer setup and a timing analysis unit;

iii) a measuring unit configured to measure the intensity shifts of the 4-quadrant photodiode and correlate the signals from all 4-quadrant photodiodes.

20. The X-ray imaging system of claim 19, wherein for said phase analysis, said coupling unit is provided.

* * * * *